(12) United States Patent
Wen et al.

(10) Patent No.: US 11,543,413 B2
(45) Date of Patent: Jan. 3, 2023

(54) KIT AND METHOD FOR QUANTITATIVE DETECTION OF HBSAG

(71) Applicants: XIAMEN INNODX BIOTECH CO., LTD, Xiamen (CN); XIAMEN UNIVERSITY, Xiamen (CN)

(72) Inventors: Shunhua Wen, Xiamen (CN); Liuwei Song, Xiamen (CN); Zuxing Weng, Xiamen (CN); Haijun Lin, Xiamen (CN); Feihai Xu, Xiamen (CN); Xudong Sun, Xiamen (CN); Shengxiang Ge, Xiamen (CN)

(73) Assignees: XIAMEN INNODX BIOTECH CO., LTD, Fujian (CN); XIAMEN UNIVERSITY, Fujian (CN)

( * ) Notice: Subject to any disclaimer, the term of this patent is extended or adjusted under 35 U.S.C. 154(b) by 330 days.

(21) Appl. No.: 16/768,848

(22) PCT Filed: Nov. 30, 2018

(86) PCT No.: PCT/CN2018/118494
§ 371 (c)(1),
(2) Date: Jun. 1, 2020

(87) PCT Pub. No.: WO2019/109864
PCT Pub. Date: Jun. 13, 2019

(65) Prior Publication Data
US 2021/0164981 A1 Jun. 3, 2021

(30) Foreign Application Priority Data
Dec. 4, 2017 (CN) .......................... 201711258416.3

(51) Int. Cl.
*G01N 33/576* (2006.01)
*G01N 33/543* (2006.01)

(52) U.S. Cl.
CPC ... *G01N 33/5764* (2013.01); *G01N 33/54366* (2013.01)

(58) Field of Classification Search
CPC ......... G01N 33/5764; G01N 33/54366; G01N 33/68; G01N 33/576
See application file for complete search history.

(56) References Cited

U.S. PATENT DOCUMENTS 10,352,937 B2 * 7/2019 Yamagaito ......... G01N 33/5761
2009/0098531 A1 4/2009 Coleman et al.
2009/0280474 A1 11/2009 Martin et al.

FOREIGN PATENT DOCUMENTS

CN 1997895 A 7/2007
CN 101023098 A 8/2007
(Continued)

OTHER PUBLICATIONS

Getz et al., "A Comparison between the Sulfhydryl Reductants Tris(2-carboxyethyl)phosphine and Dithiothreitol for Use in Protein Biochemistry", Analytical Biochemistry, 1999, 273: 73-80.

*Primary Examiner* — David P Porta
*Assistant Examiner* — Fani Polyzos Boosalis
(74) *Attorney, Agent, or Firm* — James S. Keddie; Bozicevic, Field & Francis LLP

(57) ABSTRACT

A kit for quantitatively detecting HBsAg and a method for quantitatively detecting an HBsAg content in a sample containing HBsAg. The kit comprises a first antibody specifically binding to HBsAg and a reagent composition. The reagent composition comprises tris(2-carboxyethyl)phosphine hydrochloride (TCEP) and urea.

18 Claims, 2 Drawing Sheets

(56) References Cited

FOREIGN PATENT DOCUMENTS

| CN | 102081018 A | 6/2011 |
|---|---|---|
| CN | 106443000 A | 2/2017 |
| EP | 0154902 A2 | 9/1985 |
| EP | 3719499 A1 | 10/2020 |
| WO | WO 2004038417 A1 | 5/2004 |

* cited by examiner

KIT AND METHOD FOR QUANTITATIVE DETECTION OF HBSAG

CROSS-REFERENCE TO RELATED APPLICATIONS

This application is a § 371 national phase of International Application No. PCT/CN2018/118494, filed on Nov. 30, 2018, which claims the benefit of Chinese Application No. 201711258416.3, filed on Dec. 4, 2017, which applications are incorporated by reference herein.

TECHNICAL FIELD

The present application relates to the fields of virology and immunology. Specifically, the present application relates to a kit for quantitatively detecting HBsAg. In addition, the present application also relates to a method for quantitatively detecting the amount of HBsAg in a sample containing HBsAg.

BACKGROUND ART

Hepatitis B virus (HBV) infection, especially chronic hepatitis B virus infection, is one of the most serious global public health problems. At present, there are more than 350 million people infected with chronic hepatitis B virus worldwide. Chronic hepatitis B virus infection can cause liver diseases such as chronic hepatitis B (CHB), liver cirrhosis (Liver cirrhosis, LC), and primary hepatocellular carcinoma (HCC). The deaths caused by chronic hepatitis B virus infection and the diseases induced thereby are more than one million worldwide each year (Dienstag J L. Hepatitis B virus infection. N Engl J Med 2008; 359: 1486-1500).

Hepatitis B virus surface antigen (HBsAg) is an outer membrane protein of HBV. HBsAg is clinically the most important diagnostic marker of HBV infection. Long-term presence of HBsAg indicates chronic HBV infection. In recent years, the clinical significance of HBsAg quantitative detection has been gradually revealed and the detection is widely used.

The decrease of HBsAg during the treatment with nucleoside analogs is consistent with the decrease of HBV DNA (Chen Xiangsheng, Liao Wenjun. Clinical diagnostic significance of quantitative detection of hepatitis B HBsAg, [J]. Journal of Hubei College of Traditional Chinese Medicine, 2009, 11 (2): 21-23). When drug-resistant strains appear, serum HBsAg level will increase and often precede HBV DNA rebound and biochemical breakthrough (an increase in ALT level) (Chen Xiangsheng, Liao Wenjun. Clinical diagnostic significance of quantitative detection of hepatitis B HBsAg, [J]. Journal of Hubei College of Traditional Chinese Medicine, 2009, 11(2): 21-23; and Chen Ruilie, et al. Relationship between serum HBV DNA level and liver function and immune parameters in patients with severe hepatitis B, [J]. China Journal of Primary Medicine, 2006, 13 (9): 1449-1450).

In detection and prediction of response to interferon therapy, a rapid appearance with a significant decrease of the quantitative level of HBsAg at an early stage of treatment, or a lower baseline level of HBsAg before treatment, is conducive to obtaining sustained virological response (SVR) and HBeAg seroconversion (Luo Weimin, Wang Chaohui, Liu Zhongjing. The relationship and significance of HBV DNA and its five detection indexes, [J]. Qilu Journal of Medicine, 2009, 24 (1): 4-5; and Liu Can, Weng Yirui, Chen Yongdong. Comparative study of HBsAg quantification with HBV-DNA and hepatitis B marker patterns in patients with hepatitis B, [J]. Fujian Journal of Medicine, 2006, 28 (4): 124-125). During the treatment of HBeAg-positive patients with PEG-IFN, it is an important predictive indicator for HBeAg seroconversion that HBsAg quantification is <1500 IU/mL at week 12 of treatment, while it is a potent predictive indicator for non-responding that HBsAg quantification is >20,000 IU/mL at week 12 of treatment (Piratvisuth T, et al. Hepatol Int. 2013 June; 7(2): 429-36.; and Sonneveld M J, et al. Hepatology. 2010; 52: 1251-1257). During the treatment of HBeAg-negative patients with PEG-IFN, no decrease of HBsAg concentration with an HBV DNA decline of less than 2 Log 10 IU/ml is a potent predictive indicator for non-response to treatment, indicating that the treatment can be stopped and replaced with other drugs (Rijckborst V, et al. Hepatology 2010, 52: 454-461; and Rijckborst V, et al. Journal of hepatology 2012, 56: 1006-1011).

The current HBsAg quantitative reagents use the "sandwich" detection method of "coated antibody-antigen-labeled antibody". The difference between different reagents mainly lies in the difference of the coating mediums and labels. In addition, the quantitative ranges of different reagents are also different in certain extent. For example, Roche reagent uses biotin and rare metal "ruthenium" to respectively label the two antibodies for detecting the antigen, and then captures the double-antibody sandwich complex formed by the reaction between the antigen and the antibodies via an avidin-labeled magnetic particle so as to detect an electrochemical signal, in which the detection range of the reagent is 0 to 130 IU/mL under a condition without diluting the sample; while for Abbott reagent, an antibody is directly coated on a magnetic particle, and the other antibody is labeled with acridinium ester, the double-antibody sandwich complex is formed by reacting with the sample, and the chemiluminescence signal is detected, in which the detection range of the reagent is 0 to 250 IU/mL under a condition without diluting the sample.

However, most patients with chronic hepatitis B currently have an HBsAg quantitative level of above 100 IU/ml (Jaroszewicz J, et al. Journal of Hepatology, 2010, 52 (4): 514-522; and Nguyen T, et al. Journal of Hepatology, 2010 52 (4): 508-513). Therefore, for most clinical samples, the quantitative values of the samples can be detected by use of the existing commercial reagents only when the samples are diluted before testing. However, due to the large dilution fold, the dilution operation has to be repeated for several times to dilute the sample, and the dilution process takes time. Taking Abbott reagent as an example, when manually making a 500-fold dilution, 25 µl of a sample is firstly added to 475 µl of a dilution solution to make a 20-fold dilution, and then 20 µl of the 1:20 diluted sample is added to 480 µl of the dilution solution to achieve the 500-fold dilution, and manual dilution reduces accuracy. Even the automatic dilution by a fully automatic instrument also requires multiple dilution operations, and the larger the dilution fold, the lower the detection throughput of the instrument, which reduces the detection accuracy.

Therefore, there is a need in the art to develop a HBsAg quantitative detection method that does not require sample dilution and has a higher upper limit of detection, in order to achieve a simpler, faster and more accurate determination of HBsAg content in a clinical sample.

CONTENTS OF THE INVENTION

After a lot of experimental researches, the inventors have unexpectedly found that during the quantitative detection of HBsAg, the upper limit of detection could be significantly increased to 100,000 IU/mL when the sample to be tested was not diluted, by using a specific reagent composition, so that most clinical samples could fall into the detection range. Based on this finding, the inventors have developed a new HBsAg quantitative detection kit and detection method.

Kit

Therefore, one aspect of the present invention provides a kit, comprising a first antibody capable of specifically binding to HBsAg and a reagent composition, and the reagent composition comprising tris(2-carboxyethyl)phosphine hydrochloride (TCEP) and urea.

In certain preferred embodiments, the reagent composition further comprises one or more agents selected from the group consisting of a non-ionic surfactant, an inorganic salt, and a buffer.

In certain preferred embodiments, the non-ionic surfactant is selected from the group consisting of Chaps, sulfobetaine type surfactants, Triton type detergents, Tween type detergents and any combination thereof. In certain preferred embodiments, the non-ionic surfactant is selected from the group consisting of SB14, SB16, Tween-20, Tween-40, Triton X-100, and any combination thereof. In certain preferred embodiments, the non-ionic surfactant is Triton X-100 and/or Tween-20.

In certain preferred embodiments, the inorganic salt is selected from $NH_4SO_4$, NaCl, and the like.

In certain preferred embodiments, the buffer is a carbonate buffer.

In certain preferred embodiments, the reagent composition comprises TCEP, urea, and a balance of water.

In certain preferred embodiments, the reagent composition comprises TCEP, urea, an inorganic salt (e.g., NaCl), and a balance of water.

In certain preferred embodiments, the reagent composition comprises TCEP, urea, an inorganic salt (e.g., NaCl), a non-ionic surfactant (e.g., Tween-20), and a balance of water.

In certain preferred embodiments, the reagent composition comprises TCEP, urea, an inorganic salt (e.g., NaCl), a non-ionic surfactant (e.g., Tween-20), a buffer (e.g., a carbonate buffer), and a balance of water.

In certain preferred embodiments, in the reagent composition, TCEP is present in an amount of 1 to 100 mM (e.g., 1 to 50 mM, 10 to 50 mM, 20 to 50 mM, or 30 to 50 mM; e.g., 40 mM); urea is present in an amount of 0.5 to 8 M (e.g., 1 to 8 M, 1 to 6 M, or 2 to 6 M; for example, 2 M); the non-ionic surfactant is present in an amount of 0 to 10% (v/v) (e.g., 0.1 to 1%, for example 0.1%); the inorganic salt is present in an amount of 0.5 to 8 M (e.g., 0.5 to 1 M, for example 0.6 mM); and the buffer is present in an amount of 0 to 200 mM (e.g., 50 to 200 mM, or 50 to 150 mM; for example, 100 mM).

In certain preferred embodiments, the reagent composition comprises 40 mM TCEP and 2 M urea. In certain exemplary embodiments, the reagent composition consists of the following components: 40 mM TCEP, 2 M urea, 600 mM NaCl, 100 mM carbonate buffer (pH 9.6), 0.1% Tween-20 (v/v), and a balance of water (e.g., deionized water).

In certain preferred embodiments, the first antibody is a monoclonal antibody. In certain exemplary embodiments, the first antibody is selected from the group consisting of 15D1 (M1056), 42B6 (M1058), 6C10 (M10510), 2C1 (M1057), SF (M10517), and any combination thereof, all from Xiamen Wantai Canghai Biotechnology Co., Ltd.

In certain preferred embodiments, the kit further comprises a detection reagent capable of recognizing and binding to HBsAg. Such detection reagent is well known in the art and includes, but is not limited to, antibodies, targeting polypeptides, or aptamers capable of specifically binding to HBsAg. In certain exemplary embodiments, the detection reagent is a secondary antibody capable of specifically binding to HBsAg. In certain exemplary embodiments, the second antibody is a polyclonal antibody.

In certain preferred embodiments, the detection reagent bears a detectable label, such as an enzyme (e.g., horseradish peroxidase or alkaline phosphatase), a chemiluminescent reagent (e.g., an acridinium ester compound), or a fluorescent dye. In certain exemplary embodiments, when the detectable label is an enzyme, the kit may further comprise a coloring solution, such as o-phenylenediamine (OPD), tetramethylbenzidine (TMB), ABTS or luminol compound for horseradish peroxidase, or p-nitrophenyl phosphate (p-NPP) or AMPPD for alkaline phosphatase.

In certain preferred embodiments, the kit further comprises a solid support, and optionally further comprises a coating reagent such as a coating buffer (e.g., carbonate buffer, phosphate buffer, Tris-HCL buffer, or borate buffer) for coating the first antibody on the solid support. In certain preferred embodiments, the solid support comprises a plate with recessed well, tube, particle (e.g., latex particle) or membrane (e.g., nitrocellulose membrane) made of or coated with a polymer material (e.g., polyvinyl chloride, polystyrene, polyacrylamide, or cellulose), or a magnetic bead pre-coated with a functional group (e.g., amino, carboxyl, biotin, or avidin). In certain exemplary embodiments, the solid support is a microtiter plate (e.g., a microwell plate or an ELISA plate). In certain exemplary embodiments, the solid support is a magnetic bead. The methods for coating a protein or polypeptide on a solid support are well known in the art, such as physical adsorption, covalent coupling via surface with amino groups or carboxylic groups, or mediation binding achieved by avidin-biotin system, polylysine pre-coated surface, protein A or protein G pre-coated surface.

In certain preferred embodiments, the first antibody is coated on a surface of the solid support. In certain exemplary embodiments, the first antibody is coated on a surface of a microtiter plate (e.g., a microwell plate or an ELISA plate). In certain exemplary embodiments, the first antibody is coated on a surface of a magnetic bead.

In certain preferred embodiments, the kit further comprises one or more reagents or devices selected from the group consisting of: standards (e.g., a series of samples containing different known amounts of HBsAg); a positive control sample (e.g., a sample containing a known amount of HBsAg); a negative control sample (e.g., a sample containing no HBsAg); a stop solution (e.g., sulfuric acid, hydrochloric acid or sodium hydroxide solution) for stopping a color reaction of substrate catalyzed by enzyme; a blocking solution for inhibiting non-specific binding; and, a blood collection device (e.g., a pyrogen-free vacuum blood collection tube).

Reaction System

In another aspect, the present invention provides a reaction system, comprising HBsAg, a first antibody capable of specifically binding to HBsAg, and a reagent composition, the reagent composition comprising tris(2-carboxyethyl)phosphine hydrochloride (TCEP) and urea.

In certain preferred embodiments, the reagent composition further comprises one or more agents selected from the group consisting of a non-ionic surfactant, an inorganic salt, and a buffer.

In certain preferred embodiments, the non-ionic surfactant is selected from the group consisting of Chaps, sulfobetaine type surfactants, Triton type detergents, Tween type detergents, and any combination thereof. In certain preferred embodiments, the non-ionic surfactant is selected from the group consisting of SB14, SB16, Tween-20, Tween-40, Triton X-100, and any combination thereof. In certain preferred embodiments, the non-ionic surfactant is Triton X-100 and/or Tween-20.

In certain preferred embodiments, the inorganic salt is selected from $NH_4SO_4$, NaCl, and the like.

In certain preferred embodiments, the buffer is a carbonate buffer.

In certain preferred embodiments, the reagent composition comprises TCEP, urea, and a balance of water.

In certain preferred embodiments, the reagent composition comprises TCEP, urea, an inorganic salt (e.g., NaCl), and a balance of water.

In certain preferred embodiments, the reagent composition comprises TCEP, urea, an inorganic salt (e.g., NaCl), a non-ionic surfactant (e.g., Tween-20), and a balance of water.

In certain preferred embodiments, the reagent composition comprises TCEP, urea, an inorganic salt (e.g., NaCl), a non-ionic surfactant (e.g., Tween-20), a buffer (e.g., a carbonate buffer), and a balance of water.

In certain preferred embodiments, in the reagent composition, TCEP is present in an amount of 1 to 100 mM (e.g., 1 to 50 mM, 10 to 50 mM, 20 to 50 mM, or 30 to 50 mM; e.g., 40 mM);
urea is present in an amount of 0.5 to 8 M (e.g., 1 to 8 M, 1 to 6 M, or 2 to 6 M; for example, 2 M); the non-ionic surfactant is present in an amount of 0 to 10% (v/v) (e.g., 0.1 to 1%, for example 0.1%); the inorganic salt is present in an amount of 0.5 to 8 M (e.g., 0.5 to 1 M, for example 0.6 mM); and the buffer is present in an amount of 0 to 200 mM (e.g., 50 to 200 mM, or 50 to 150 mM; for example, 100 mM).

In certain preferred embodiments, the reagent composition comprises 40 mM TCEP and 2M urea. In certain exemplary embodiments, the reagent composition consists of the following components: 40 mM TCEP, 2M urea, 600 mM NaCl, 100 mM carbonate buffer (pH 9.6), 0.1% Tween-20 (v/v), and a balance of water (e.g., deionized water).

In certain preferred embodiments, the first antibody is a monoclonal antibody. In certain exemplary embodiments, the first antibody is selected from the group consisting of 15D1 (M1056), 42B6 (M1058), 6C10 (M10510), 2C1 (M1057), SF (M10517), and any combination thereof, all from Xiamen Wantai Canghai Biotechnology Co., Ltd.

Detection Method and Use

In another aspect, the present invention provides a method for quantitatively detecting the amount of HBsAg in a sample containing HBsAg, which comprises the following steps:

(1) contacting the sample with a first antibody capable of specifically binding to HBsAg in a reagent composition to obtain an immune complex;

(2) determining the amount of the immune complex obtained in step (1);

wherein, in step (1), the reagent composition comprises TCEP and urea.

In certain preferred embodiments, the method of the present invention is used for non-diagnostic purposes. In such embodiments, since the sample to be tested is known to contain HBsAg, that is, the subject of the sample already has a diagnostic result before the method of the present invention is used for testing, the method of the present invention is not helpful for the diagnosis steps of the sample. It can be seen that the direct purpose of the method of the present invention is not to obtain the diagnosis result of the subject of the sample, but to perform further accurate quantitative detection on the sample with known diagnostic information.

In certain preferred embodiments, the sample is a blood sample, such as whole blood, plasma or serum. In certain preferred embodiments, the blood sample is undiluted.

In certain preferred embodiments, in step (1), the reagent composition further comprises one or more reagents selected from the group consisting of a non-ionic surfactant, an inorganic salt, and a buffer.

In certain preferred embodiments, the non-ionic surfactant is selected from the group consisting of Chaps, sulfobetaine type surfactants, Triton type detergents, Tween type detergents and any combination thereof. In certain preferred embodiments, the non-ionic surfactant is selected from the group consisting of SB14, SB16, Tween-20, Tween-40, Triton X-100, and any combination thereof. In certain preferred embodiments, the non-ionic surfactant is Triton X-100 and/or Tween-20.

In certain preferred embodiments, the inorganic salt is selected from $NH_4SO_4$, NaCl, and the like.

In certain preferred embodiments, the buffer is a carbonate buffer.

In certain preferred embodiments, the reagent composition comprises TCEP, urea, and a balance of water.

In certain preferred embodiments, the reagent composition comprises TCEP, urea, an inorganic salt (e.g., NaCl), and a balance of water.

In certain preferred embodiments, the reagent composition comprises TCEP, urea, an inorganic salt (e.g., NaCl), a non-ionic surfactant (e.g., Tween-20), and a balance of water.

In certain preferred embodiments, the reagent composition comprises TCEP, urea, an inorganic salt (e.g., NaCl), a non-ionic surfactant (e.g., Tween-20), a buffer (e.g., a carbonate buffer), and a balance of water.

In certain preferred embodiments, in the reagent composition, TCEP is present in an amount of 1 to 100 mM (e.g., 1 to 50 mM, 10 to 50 mM, 20 to 50 mM, or 30 to 50 mM; e.g., 40 mM); urea is present in an amount of 0.5 to 8 M (e.g., 1 to 8 M, 1 to 6 M, or 2 to 6 M; for example, 2M); the non-ionic surfactant is present in an amount of 0 to 10% (v/v) (e.g., 0.1 to 1%, for example 0.1%); the inorganic salt is present in an amount of 0.5 to 8 M (e.g., 0.5 to 1 M, for example 0.6 mM); and the buffer is present in an amount of 0 to 200 mM (e.g., 50 to 200 mM, or 50 to 150 mM; for example, 100 mM).

In certain preferred embodiments, the reagent composition comprises 40 mM TCEP and 2M urea. In certain exemplary embodiments, the reagent composition consists of the following components: 40 mM TCEP, 2M urea, 600 mM NaCl, 100 mM carbonate buffer (pH 9.6), 0.1% Tween-20 (v/v), and a balance of water (e.g., deionized water).

In certain preferred embodiments, in step (2), the amount of the immune complex is determined by immunological detection. In certain preferred embodiments, the immunological detection is an enzyme immunoassay or a chemiluminescent immunoassay. In certain exemplary embodiments, the immunological detection is selected from CLEIA and CLIA. In certain exemplary embodiments, in step (2), the amount of the immune complex is detected using a second antibody capable of specifically binding to HBsAg, and the second antibody carries a detectable label, such as an enzyme (e.g., horseradish peroxidase or alkaline phosphatase), a chemiluminescent reagent (e.g. an acridinium ester compound) or a fluorescent dye. In such embodiments, the second antibody and the immune complex obtained in step (1) are capable of forming an "antibody-antigen-antibody" sandwich complex.

In some preferred embodiments, a step of washing the immune complex to remove unreacted substance is further comprised before step (2).

In certain preferred embodiments, the first antibody is coated on a surface of a solid support. In certain preferred embodiments, the solid support comprises a plate with recessed well, tube, particle (e.g., latex particle) or membrane (e.g., nitrocellulose membrane) made of or coated with a polymer material (e.g., polyvinyl chloride, polystyrene, polyacrylamide, or cellulose), or a magnetic bead pre-coated with a functional group (e.g., amino, carboxyl, biotin, or avidin). In certain exemplary embodiments, the first antibody is coated on a surface of a microtiter plate (e.g., a microwell plate or an ELISA plate). In certain exemplary embodiments, the first antibody is coated on a surface of a magnetic bead.

In another aspect, the invention relates to use of a reagent composition in the manufacture of a kit for detecting the amount of HBsAg in a blood sample of a subject, wherein the reagent composition comprises tris(2-carboxyethyl) phosphine hydrochloride (TCEP) and urea.

In certain preferred embodiments, the reagent composition further comprises one or more agents selected from the group consisting of a non-ionic surfactant, an inorganic salt, and a buffer.

In certain preferred embodiments, the non-ionic surfactant is selected from the group consisting of Chaps, sulfobetaine type surfactants, Triton type detergents, Tween type detergents and any combination thereof. In certain preferred embodiments, the non-ionic surfactant is selected from the group consisting of SB14, SB16, Tween-20, Tween-40, Triton X-100, and any combination thereof. In certain preferred embodiments, the non-ionic surfactant is Triton X-100 and/or Tween-20.

In certain preferred embodiments, the inorganic salt is selected from $NH_4SO_4$, NaCl, and the like.

In certain preferred embodiments, the buffer is a carbonate buffer.

In certain preferred embodiments, the reagent composition comprises TCEP, urea, and a balance of water.

In certain preferred embodiments, the reagent composition comprises TCEP, urea, an inorganic salt (e.g., NaCl), and a balance of water.

In certain preferred embodiments, the reagent composition comprises TCEP, urea, an inorganic salt (e.g., NaCl), a non-ionic surfactant (e.g., Tween-20), and a balance of water.

In certain preferred embodiments, the reagent composition comprises TCEP, urea, an inorganic salt (e.g., NaCl), a non-ionic surfactant (e.g., Tween-20), a buffer (e.g., a carbonate buffer), and a balance of water.

In certain preferred embodiments, in the reagent composition, TCEP is present in an amount of 1 to 100 mM (e.g., 1 to 50 mM, 10 to 50 mM, 20 to 50 mM, or 30 to 50 mM; e.g., 40 mM);

urea is present in an amount of 0.5 to 8 M (e.g., 1 to 8 M, 1 to 6 M, or 2 to 6 M; for example, 2M); the non-ionic surfactant is present in an amount of 0 to 10% (v/v) (e.g., 0.1 to 1%, for example 0.1%); the inorganic salt is present in an amount of 0.5 to 8 M (e.g., 0.5 to 1 M, for example 0.6 mM); and the buffer is present in an amount of 0 to 200 mM (e.g., 50 to 200 mM, or 50 to 150 mM; for example, 100 mM).

In certain preferred embodiments, the reagent composition comprises 40 mM TCEP and 2M urea. In certain exemplary embodiments, the reagent composition consists of the following components: 40 mM TCEP, 2M urea, 600 mM NaCl, 100 mM carbonate buffer (pH 9.6), 0.1% Tween-20 (v/v), and a balance of water (e.g., deionized water).

In certain preferred embodiments, the kit further comprises a first antibody specifically binding to HBsAg. In certain preferred embodiments, the first antibody is a monoclonal antibody. In certain exemplary embodiments, the first antibody is selected from the group consisting of 15D1 (M1056), 42B6 (M1058), 6C10 (M10510), 2C1 (M1057), SF (M10517), and any combination thereof, all from Xiamen Wantai Canghai Biotechnology Co., Ltd.

In certain preferred embodiments, the present invention relates to use of the reagent composition and the first antibody in the manufacture of a kit for detecting the amount of HBsAg in a blood sample of a subject.

In certain preferred embodiments, the kit further comprises a detection reagent capable of recognizing and binding to HBsAg. Such detection reagent is well known in the art and includes, but is not limited to, antibodies, targeting polypeptides, or aptamers capable of specifically binding to HBsAg. In certain exemplary embodiments, the detection reagent is a secondary antibody capable of specifically binding to HBsAg. In certain exemplary embodiments, the second antibody is a polyclonal antibody.

In certain preferred embodiments, the detection reagent bears a detectable label, such as an enzyme (e.g., horseradish peroxidase or alkaline phosphatase), a chemiluminescent reagent (e.g., an acridinium ester compound), or a fluorescent dye. In certain exemplary embodiments, when the detectable label is an enzyme, the kit may further comprises a coloring solution, such as o-phenylenediamine (OPD), tetramethylbenzidine (TMB), ABTS or luminol compound for horseradish peroxidase, or p-nitrophenyl phosphate (p-NPP) or AMPPD for alkaline phosphatase.

In certain preferred embodiments, the kit further comprises a solid support, optionally further comprising a coating reagent such as a coating buffer (e.g., carbonate buffer, phosphate buffer, Tris-HCL buffer, or borate buffer) for coating the first antibody on the solid support. In certain preferred embodiments, the solid support comprises a plate with recessed well, tube, particle (e.g., latex particle) or membrane (e.g., nitrocellulose membrane) made of or coated with a polymer material (e.g., polyvinyl chloride, polystyrene, polyacrylamide, or cellulose), or a magnetic bead pre-coated with a functional group (e.g., amino, carboxyl, biotin, or avidin). In certain exemplary embodiments, the solid support is a microtiter plate (e.g., a microwell plate or an ELISA plate). In certain exemplary embodiments, the solid-phase support is a magnetic bead. The methods for coating a protein or polypeptide on a solid support are well known in the art, such as physical adsorption, covalent coupling via surface with amino groups or carboxylic groups, or mediation binding achieved by avidin-biotin system, polylysine pre-coated surface, protein A or protein G pre-coated surface.

In certain preferred embodiments, the first antibody is coated on a surface of the solid support. In certain exemplary embodiments, the first antibody is coated on a surface of a microtiter plate (e.g., a microwell plate or an ELISA plate). In certain exemplary embodiments, the first antibody is coated on a surface of a magnetic bead.

In certain preferred embodiments, the kit further comprises one or more reagents or devices selected from the group consisting of: standards (e.g., a series of samples containing different known amounts of HBsAg); a positive control sample (e.g., a sample containing a known amount of HBsAg); a negative control sample (e.g., a sample containing no HBsAg); a stop solution (e.g., sulfuric acid, hydrochloric acid or sodium hydroxide solution) for stopping a color reaction of substrate catalyzed by enzyme; a blocking solution for inhibiting non-specific binding; and, a blood collection device (e.g., a pyrogen-free vacuum blood collection tube).

In certain preferred embodiments, the kit detects the amount of HBsAg in a blood sample of a subject by a method comprising the following steps:

(1) contacting the blood sample with the first antibody in the reagent composition to obtain an immune complex;

(2) determining the amount of the immune complex obtained in step (1);

wherein, in step (1), the blood sample is undiluted.

In certain preferred embodiments, in step (2), the amount of the immune complex is determined by immunological detection. In certain preferred embodiments, the immunological detection is an enzyme immunoassay or a chemiluminescent immunoassay. In certain exemplary embodiments, the immunological detection is selected from CLEIA and CLIA. In certain exemplary embodiments, in step (2), the amount of the immune complex is detected using a second antibody capable of specifically binding to HBsAg, and the second antibody carries a detectable label, such as an enzyme (e.g., horseradish peroxidase or alkaline phosphatase), a chemiluminescent reagent (e.g., an acridinium ester compound), or a fluorescent dye. In such embodiments, the second antibody and the immune complex obtained in step (1) are capable of forming an "antibody-antigen-antibody" sandwich complex.

In some preferred embodiments, a step of washing the immune complex to remove unreacted substance is further comprised before step (2).

In certain preferred embodiments, the subject has HBV infection or a disease associated with HBV infection (e.g., hepatitis B).

In certain preferred embodiments, the blood sample is selected from the group consisting of whole blood, plasma, and serum.

Definition of Terms

In the present invention, unless otherwise stated, scientific and technical terms used herein have meanings commonly understood by those skilled in the art. Moreover, the virological, biochemical, and immunological laboratory procedures as used herein are all routine procedures that are widely used in the corresponding fields. Meanwhile, in order to better understand the present invention, definitions and explanations of related terms are provided below.

As used herein, the term "HBsAg" refers to a surface antigen major protein of hepatitis B virus (HBV), which is well known to those skilled in the art (see, for example, NCBI GENBANK database accession number: AAF24729.1).

As used herein, the term "specifically bind" or "specific binding" refers to a non-random binding reaction between two molecules (i.e., a binding molecule and a target molecule), such as a reaction between an antibody and an antigen to which it is directed. The binding affinity between two molecules can be described by a $K_D$ value. $K_D$ value refers to a dissociation constant obtained from a ratio of kd (the dissociation rate of the specific binding molecule-target molecule interaction; also known as koff) to ka (the association rate of the specific binding molecule-target molecule interaction; also known as kon), or refers to kd/ka expressed as molar concentration (M). The smaller the $K_D$ value, the closer the two molecules bind, and the higher the affinity. In some embodiments, an antibody that specifically binds to an antigen (or an antibody specific to an antigen) means that the antibody binds to the antigen with an affinity ($K_D$) of less than about $10^{-5}$ M, such as less than about $10^{-6}$ M, $10^{-7}$ M, $10^{-8}$ M, $10^{-9}$ M, or $10^{-10}$ M or less. The $K_D$ value can be determined by a method well known in the art, for example by surface plasmon resonance (SPR) in a BIACORE instrument.

As used herein, the term "immunological detection" refers to an assay using specific interaction/binding affinity between antigen-antibody, which is generally useful for detecting the presence or level of a specific antigen or antibody in a sample. Such immunological detection is well known to those skilled in the art and includes, but is not limited to, enzyme immunoassay (EIA), chemiluminescence immunoassay (CLIA), radioimmunoassay (RIA), fluorescence immunoassay (FIA), Western blotting, immunoturbidimetry, surface plasmon resonance, etc. In certain embodiments, the immunological detection is an enzyme immunoassay (EIA), such as an ELISA, Elispot, or CLEIA. For a detailed description of the immunological detection, see, for example, Fundamental Immunology, Ch. 7 Paul, W., ed., 2nd edition, Raven Press, N.Y. (1989).

As used herein, the term "detectable label" refers to any composition that can be detected by fluorescent, spectroscopic, photochemical, biochemical, immunological, electrical, optical, or chemical means. In the present invention, it is particularly preferred that such a label can be suitable for immunological detection (e.g., enzyme-linked immunoassay, radioimmunoassay, fluorescent immunoassay, chemiluminescence immunoassay, etc.). Such label is well known in the art and includes, but is not limited to, an enzyme (e.g., horseradish peroxidase, alkaline phosphatase, β-galactosidase, urease, glucose oxidase, etc.), a radionuclide (e.g., 3H, 125I, 35S, 14C, or 32P), a fluorescent dye (e.g., fluorescein isothiocyanate (FITC), fluorescein, tetramethylrhodamine isothiocyanate (TRITC), phycoerythrin (PE), Texas Red, Rhodamine, quantum dot or cyanine dye derivatives (e.g., Cy7, Alexa 750)), an acridinium ester compound, a magnetic bead (e.g., Dynabeads®), a calorimetric label such as a colloidal gold or colored glass or plastic bead (e.g., polystyrene, polypropylene, latex, etc.), and a biotin used to bind avidin (e.g., streptavidin) modified by the above label. Patents that teach the use of such label include, but are not limited to, U.S. Pat. Nos. 3,817,837; 3,850,752; 3,939,350; 3,996,345; 4,277,437; 4,275,149; and 4,366,241 (all incorporated herein by reference). The label encompassed in the present invention can be detected by a method known in the art. For example, a radioactive label can be detected using photographic film or a scintillation counter, and a fluorescent label can be detected using a photodetector to detect the emitted light. An enzyme label is generally detected by providing a substrate to the enzyme and detecting a reaction product produced by the effect of the enzyme on the substrate, and a calorimetric label is detected by simply visualizing the colored label.

As used herein, the expression "detection reagent capable of recognizing and binding to HBsAg" refers to a substance capable of specifically binding to HBsAg. Such substance is known in the art, or can be prepared by a method known in the art, including for example antibodies, targeting polypeptides, or aptamers. In general, it is particularly preferred that such reagent is capable of determining the amount of HBsAg in a sample by immunological detection. The use of immunological detection is particularly advantageous because it takes advantage of the specific interaction/binding affinity between the antigen-antibody. Therefore, as long as a reagent retains the reactivity of specifically binding to HBsAg, the reagent can be used to determine the amount of HBsAg in a sample by immunological detection (that is, the reagent can be used as a detection reagent capable of recognizing and binding to HBsAg). Various reagents that retain reactivity of specifically binding to HBsAg are readily conceivable and available to those skilled in the art, and include, but are not limited to, anti-HBsAg antibodies or antigen-binding fragments thereof, such as anti-HBsAg polyclonal antibodies or monoclonal antibodies.

As used herein, the term "antibody" refers to an immunoglobulin molecule that typically consists of two pairs of polypeptide chains, each pair having one "light" (L) chain and one "heavy" (H) chain. Antibody light chains can be classified into κ and λ light chains. Heavy chains can be classified as μ, δ, γ, α, or ε, and the isotypes of antibody are defined as IgM, IgD, IgG, IgA, and IgE, respectively. Within the light and heavy chains, the variable and constant regions are linked by a "J" region of about 12 or more amino acids, and the heavy chain also contains a "D" region of about 3 or more amino acids. Each heavy chain is composed of a heavy chain variable region (VH) and a heavy chain constant region (CH). The heavy chain constant region consists of 3 domains (CH1, CH2, and CH3). Each light chain is composed of a light chain variable region (VL) and a light chain constant region (CL). The light chain constant region consists of one domain CL. The constant region of an antibody can mediate the binding of immunoglobulin to a host tissue or factor, including various cells of immune system (e.g., effector cells) and a first component (C1q) of classical complement system. The VH and VL regions can also be subdivided into regions with high denaturation (referred to as complementary determining regions (CDRs)), interspaced with relatively conservative regions called framework regions (FRs). Each of VH and VL is composed of 3 CDRs and 4 FRs arranged in the following order: FR1, CDR1, FR2, CDR2, FR3, CDR3 and FR4 from the amino terminal to the carboxy terminal. The variable regions (VH and VL) of each heavy/light chain pair form an antibody binding site, respectively. The assignment of amino acids to regions or domains follows the definition of Kabat Sequences of Proteins of Immunological Interest (National Institutes of Health, Bethesda, Md. (1987 and 1991)), or Chothia & Lesk (1987) J. Mol. Biol. 196: 901-917; Chothia et al. (1989) Nature 342: 878-883. The term "antibody" is not limited by any particular method for producing the antibody. For example, it includes, in particular, recombinant antibodies, monoclonal antibodies, and polyclonal antibodies. The antibody may be an antibody of different isotypes, for example, IgG (e.g., IgG1, IgG2, IgG3 or IgG4 subtypes), IgA1, IgA2, IgD, IgE or IgM antibodies.

As used herein, the term "Aptamer" refers to a single-stranded oligonucleotide capable of binding to a target protein of interest (e.g., HBsAg) or other biological target molecules with high affinity and high specificity. Aptamer can be folded to form a thermodynamically stable three-dimensional space structure such as stem-loop, hairpin, pseudoknot, or G-tetramer, and it specifically binds to a target protein of interest or other biological target molecules via structural complementarity, base stacking force, van der Waals force, hydrogen bonding, or electrostatic interaction. Aptamer can be DNA or RNA, and can also contain nucleic acid analogs (e.g., locked nucleic acid (LNA), peptide nucleic acid (PNA), glycol nucleic acid (GNA), or threose nucleic acid (TNA)). Methods for obtaining an aptamer that binds to a specific target protein are well known in the art, such as SELEX (Systematic evolution of ligands by exponential enrichment) screening technology.

As used herein, the term "targeting polypeptide" refers to a polypeptide molecule that can specifically bind to a target protein of interest (e.g., HBsAg). In the present invention, the targeting polypeptide may include natural amino acids, synthetic amino acids, or amino acid mimetics that function in a manner similar to naturally occurring amino acids. Naturally occurring amino acids are those encoded by genetic codes, as well as those amino acids that are later modified, for example, hydroxyproline, γ-hydroxyglutamate, O-phosphoserine, phosphothreonine, or phosphotyrosine. In the present invention, the "specificity" between the targeting polypeptide and the target protein of interest can be determined based on the affinity, and the affinity can be described by the dissociation equilibrium constant (i.e., $K_D$ value) of the targeting polypeptide and the target protein of interest to which it binds. The lower the $K_D$ value, the stronger the binding strength between the targeting polypeptide and the target protein of interest to which it binds. It is generally known in the art that $K_D$ values greater than about $10^{-3}$ M are generally considered to indicate non-binding or non-specific binding. Depending on the specific target protein of interest, the targeting polypeptide that specifically binds to the target protein can be obtained by a method known to those skilled in the art, such as screening by phage display technology or protein microarray technology.

As used herein, the expression "blood sample is undiluted" means that a blood sample has not been subjected to any dilution treatment after being obtained from a subject.

As used herein, the term "subject" includes, but is not limited to, various animals, particularly mammals, such as bovines, equines, lambs, porcines, canines, felines, rabbits, rodents (e.g., mice or rats), non-human primates (e.g., macaques or cynomolgus monkeys), or humans.

Beneficial Effects of the Invention

In clinical practice, the HBsAg level of most patients with HBV infection or hepatitis B is much higher than the upper limit of detection of the existing commercial HBsAg quantitative reagents, so that repeated dilution operations are often required for the test sample. However, the dilution process is not only time consuming, but also easy to reduce the accuracy of detection whether it is manual dilution or automatic dilution by a fully automatic instrument.

The invention provides a HBsAg quantitative detection kit comprising a specific reagent composition, and a HBsAg quantitative detection method based on the reagent composition. Compared with the prior art, the technical solution of the present invention can ensure the accuracy of detection, and its detection range can cover the distribution range of serum/plasma HBsAg concentration of most clinical samples, so that the test sample can be detected directly without being diluted, thereby greatly simplifying the operation steps.

The embodiments of the present invention will be described in detail below with reference to the drawings and examples, but those skilled in the art will understand that the following drawings and examples are only used to illustrate the present invention, rather than limiting the scope of the present invention. Various objects and advantageous aspects of the present invention will become apparent to those skilled in the art from the accompanying drawings and the following detailed description of the preferred embodiments.

SPECIFIC MODELS FOR CARRYING OUT THE INVENTION

Figure 1:
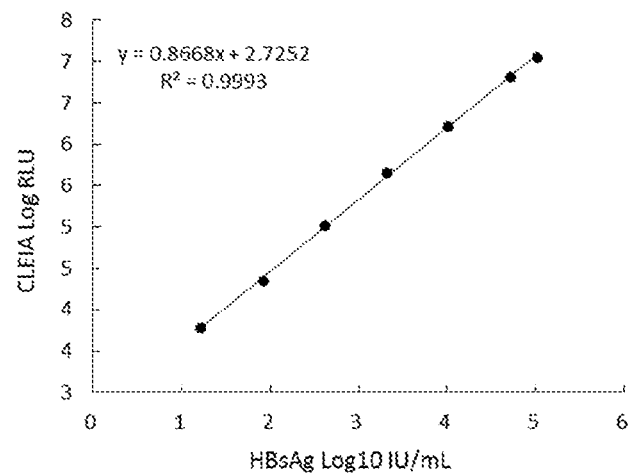
FIG. 1 shows the standard curve for HBsAg quantitation obtained in Example 1 using the kit of Preparation Example 2.

The invention will now be described with reference to the following examples which are intended to illustrate the invention without limiting it.

Unless otherwise specified, the molecular biology experimental methods and immunoassays used in the present invention basically refer to J. Sambrook et al., Molecular Cloning: A Laboratory Manual, 2nd Edition, Cold Spring Harbor Laboratory Press, 1989, and F M Ausubel et al., Short Protocols in Molecular Biology, 3rd Edition, John Wiley & Sons, Inc., 1995; the use of restriction enzymes was in accordance with conditions recommended by the product manufacturers. Those skilled in the art know that the embodiments describe the present invention by way of example and are not intended to limit the scope of the invention as claimed.

PREPARATION EXAMPLE 1

Preparation of Dissociation Solution

Formulation: 40 mM TCEP+2M urea+600 mM NaCl+100 mM CB9.6+0.1% Tween-20.

Reagents: TCEP (Cat. No. 68957), Tween-20 (Cat. No. P1379), NaCl (Cat. No. V900058), sodium bicarbonate (Cat. No. S5761-500 g), urea (V800441), and sodium carbonate (V800371) were purchased from Sigma-Aldrich.

Preparation Steps:

1. 31.8 g of sodium carbonate and 58.6 g of sodium bicarbonate were weighed, dissolved in deionized water to a volume of 1000 mL, so as to prepare a 1M carbonate buffer (CB) with a pH value of 9.6.

2. 87.66 g of NaCl was weighed, dissolved in deionized water to a volume of 500 mL, so as to prepare a 3M NaCl solution.

3. 240.24 g of urea was weighed, dissolved in deionized water to a volume of 500 mL, so as to prepare an 8M urea solution.

4. 5.733 g of TCEP was weighed, dissolved in 100 mL of deionized water, and then added with 50 mL of 1M carbonate buffer (pH 9.6), 125 mL of 8M urea, 100 mL of 3M NaCl solution, and 0.5 mL of Tween-20, mixed well and added with deionized water to a volume of 500 mL.

PREPARATION EXAMPLE 2

Preparation of HBsAg Detection Kit for Chemiluminescence Enzyme-Linked Immunoassay (CLEIA)

1. Preparation of Immobilized Antibody (1-1) Mouse anti-HBsAg monoclonal antibody (purchased from Xiamen Wantai Canghai Biotechnology Co., Ltd.) was diluted with 50 mM CB buffer (NaHCO$_3$/Na$_2$CO$_3$ buffer, final concentration 50 mM, pH 9.6) at pH 9.6, to a final concentration of 4 μg/ml to prepare a coating solution.

(1-2) 100 μL of the coating solution prepared in the previous step (1) was added to each well of a 96-well plate for chemiluminescence reaction to perform coating at 2-8° C. for 16-24 hours.

(1-3) Washing was performed once with PBST washing solution (20 mM PB7.4, 150 mM NaCl, 0.1% Tween20) to remove uncoated mouse anti-HBsAg monoclonal antibody. Then, 200 μl of blocking solution (20 mM Na$_2$HPO$_4$/NaH$_2$PO$_4$ buffer solution that had a pH of 7.4 and contained 20% infant bovine serum, 1% BSA and 1% casein) was added to each well to perform blocking at 37° C. for 2 hours; and then the blocking solution was discarded. After drying, the plate was put into an aluminum foil bag and stored at 2-8° C. for later use.

2. Preparation of Labeled Antibody

HRP labeling of anti-HBsAg polyclonal antibody was performed using a modified sodium periodate method. The following example was performed to label 10 mg of anti-HBsAg polyclonal antibody.

(2-1) Goat anti-HBsAg polyclonal antibody (5 mL) (purchased from Xiamen Wantai Canghai Biotechnology Co., Ltd., Cat. No. G1051) at a concentration of 2 mg/mL was placed in a dialysis bag, and dialyzed against 20 mM CB buffer at 4° C. for 4 hours, in which the dialysis buffer was changed every 2 hours.

(2-2) 40 mg of Horseradish Peroxidase (HRP) (Sigma-Aldrich/77332) was weighed accurately and dissolved in 2 mL of ddH$_2$O, followed by addition of 2 ml of 20 mg/mL NaIO$_4$ and reaction at room temperature for 30 minutes. 40 μL of ethylene glycol was added and reacted at 4° C. for 30 minutes to prepare an HRP activation solution (10 mg/mL, 4 mL).

(2-3) The HRP activation solution prepared in step (2-2) was added to a dialysis bag containing goat anti-HBsAg polyclonal antibody, mixed well and dialysis against 20 mM CB buffer continued at 4° C. in the dark for 6-8 hours, and the dialysis buffer was changed every 2 hours during the process.

(2-4) 0.5 mL of NaBH$_4$ solution (20 mg/mL) was prepared, added with the label reaction solution prepared in step (2-3), and mixed well. The mixture was reacted at 4° C. in the dark for 2 hours, and mixed well every 30 minutes.

(2-5) After step (2-4) was completed, the label reaction solution was loaded again into a new dialysis bag, and dialyzed against PBS buffer at 4° C. for 4 hours.

(2-6) After step (2-5) was completed, 50% saturated ammonium sulfate (50% referred to the concentration of ammonium sulfate in the dialysis bag, and the main purpose was to precipitate the goat polyclonal antibody-HRP labeled product). After centrifugation at 12000 rpm for 10 min, the supernatant was discarded, the precipitate was dissolved in 50% glycerol+10% NBS (final concentration) (NBS was the abbreviation of newborn bovine serum) by pipetting up and down, mixed well and stored at −20° C. for later use.

(2-7) The goat polyclonal antibody-HRP labeled product obtained in step (2-6) was diluted into enzyme label dilution buffer (20 mM Na$_2$HPO$_4$/NaH$_2$PO$_4$ buffer solution having a pH of 7.4 and containing 20% fetal bovine serum, 1% casein, 10% sucrose and 0.05% aminopyrine) by a dilution rate of 1/4000 by volume, to prepare an enzyme label reaction solution, and after mixing, it was stored at 2-8° C. for later use.

3. Quantitation Standards

The quantitation standards for the quantitative detection of middle- and high-concentration HBsAg samples were a series of samples containing different concentrations of hepatitis B virus surface antigen. A total of 8 standards were included, the concentrations of which were 100,000 IU/mL, 50,000 IU/mL, 10,000 IU/mL, 5,000 IU/mL, 1,000 IU/mL, 500 IU/mL, 100 IU/mL, 20 IU/mL, respectively, with a volume of 500 μl per tube. The surface antigen was provided by Xiamen Wantai Kairui Biotechnology Co., Ltd., and could be traced back to the WHO standard (Code: 00/588) issued by NIBSC. The solution used to dilute the standards could be HBsAg- and HBsAb-negative healthy blood donor's plasma or serum, or a PBS solution containing 20% newborn bovine serum.

4. Dissociation Solution

It was prepared in Preparation Example 1.

PREPARATION EXAMPLE 3

Preparation of HBsAg Detection Kit for Chemiluminescent Immunoassay (CLIA) Based on Microparticles in Tube 1. Preparation of Antibody-Labeled Magnetic Particles (1-1) 4 mg of magnetic beads (Magnosphere MS300/Carboxyl of JSR Company, Japan, particle size was 3 μm) were washed 2 times with 1 mL of activation buffer system (50 mM MES 5.0), and the supernatant was discarded. 4 mg of EDC and 4 mg of NHS reagents (both were formulated to 10 mg/mL with 50 mM MES 5.0) were added, and mixed well, followed by activation with shaking at room temperature for 20 minutes;

(1-2) The activated magnetic beads were washed 3 times with 1 mL of activation buffer system (50 mM MES 5.0) to remove excess EDC and NHS, and the supernatant was discarded. 1 mL of 50 mM phosphate buffer with a pH of 6.0 and 160 μg of a mouse anti-HBsAg monoclonal antibody were added, and mixed well, followed by reaction with shaking at room temperature for 3 hours;

(1-3) The magnetic beads obtained in (1-2) were washed 3 times with 1 ml of PBST washing solution (20 mM PB7.4, 150 mM NaCl, 0.1% Tween 20), and then added with 1 ml of blocking buffer (20 mM PB7.4, 1% glycine, 0.1% BSA, 0.05% Tween-20), and mixed well, followed by reaction with shaking at room temperature for 3 hours;

(1-4) The blocked magnetic particles obtained in step (1-3) were washed 3 times with PBST washing solution (20 mM PB7.4, 150 mM NaCl, 0.1% Tween20), and then added with 1 ml of storage buffer (20 mM Tris-HCl buffer pH 8.0, 0.5% BSA, 150 mM NaCl, 0.5% casein, 0.1% preservative), stored at 2-8° C. for later use;

(1-5) The coated magnetic particles were diluted by 10 times with storage buffer (20 mM Tris-HCl buffer pH 8.0, 0.5% BSA, 150 mM NaCl, 0.5% casein, 0.1% preservative), stored at 2-8° C. for later use.

2. Acridinium Ester Labeling of Goat Anti-HBsAg Polyclonal Antibody (2-1) 100 μg of goat anti-HBsAg polyclonal antibody was added to 300 μl of labeling buffer system (50 mM phosphate buffer, pH 8.0), added with 12 μL of acridinium ester (5 mM NHS-SAE), and reacted at room temperature for 30 minutes in the dark.

(2-2) 200 μL of stopping buffer (phosphate buffer containing 100 mM glycine, pH 8.0) was added with the labeled product prepared in step (2-1), and reacted at room temperature for 30 minutes in the dark.

(2-3) The labeled product from step (2-2) was loaded into a dialysis bag, and dialyzed against dialysis buffer (20 mM phosphate buffer, pH 7.4) at 4° C. for 6-8 hours in the dark, in which the dialysis buffer was changed every 2 hours.

(2-4) The labeled product obtained in step (2-3) was transferred into a storage tube, added with 2% BSA and 50% glycerol, and stored at −20° C. for later use.

(2-5) The acridinium ester labeled product as prepared in step (2-4) was subjected to dilution by volume ratio of 1/3000 into an acridinium ester label dilution buffer (20 mM $Na_2HPO_4/NaH_2PO_4$ buffer solution having a pH value of 7.4 and containing 0.5% BSA, 0.5% casein, 0.05% Tween-20 and 0.1% preservative) to prepare a luminescent label reaction solution, then it was stored at 2-8° C. for later use after mixing.

3. Quantitation Standards

The quantitation standards of the kit of this Preparation Example were the same as in step 3 of Preparation Example 2.

4. Dissociation Solution

It was prepared as Preparation Example 1.

EXAMPLE 1

Quantitative Detection of HBsAg in Clinical Samples

1. Experimental Reagent/Kit

Kit of Preparation Example 2.

2. Experimental Method 38 serum samples from patients with chronic hepatitis B (numbered P1 to P38) were subjected to HBsAg quantitative detection according to the following steps.

(1) Sample reaction: to each well of a coated chemiluminescent reaction plate, was added 90 μL of dissociation solution, then 10 μL of sample or standard, followed by mixing with shaking and reaction in a 37° C. incubator for 30 minutes.

(2) Enzyme label reaction: After step (1) was completed, the chemiluminescent reaction plate was washed 5 times with PBST washing solution (20 mM PB7.4, 150 mM NaCl, 0.1% Tween20) to remove the reaction dissociation solution and unreacted sample. 100 μL of the enzyme label reaction solution prepared in step (2-7) in Preparation Example 2 was added to each well, and reacted in a 37° C. incubator for 30 minutes.

(3) Luminescence reaction and measurement: After step (2) was completed, the chemiluminescent reaction plate was washed 5 times with PBST washing solution (20 mM PB7.4, 150 mM NaCl, 0.1% Tween20) to remove the excess enzyme label reaction solution. 100 μL of PICO Chemiluminescent Substrate produced by Pierce Company was added to each well, and the luminescence value (RLU) of each reaction well was immediately read with Orin II chemiluminescence detector.

(4) Generation of standard curves for quantitation: After step (3) was completed, the linear regression was performed on the measured values of the 8 quantitation standards and their corresponding concentrations to obtain a standard curve. The results were shown in FIG. 1. The results showed that the upper limit of quantification with accuracy of the above detection method was 100,000 IU/mL, the lower limit was 20 IU/mL, and the linear dynamic range thereof was 3.5 orders of magnitude. The formula for calculating HBsAg concentration from RLU measurement value was: Conc.HBsAg (IU/mL)=$10^{(Log\ 10(RLU)-2.7252)/\times 0.8668}$.

(5) Obtaining the HBsAg concentration of the samples to be tested: After the samples P1 to P38 were measured through steps (1) to (4), the corresponding RLU values of the samples were obtained. The measured values were substituted into the formula for calculating HBsAg concentration obtained in step (4) to calculate the concentrations of hepatitis B virus surface antigen in the samples.

At the same time, the quantitative detection kit for hepatitis B virus surface antigen of Roche (100 tests/box, Cat. No.: 07143737190) and the quantitative detection kit for hepatitis B virus surface antigen of Abbott (100 tests/box, Cat. No.: 6C36) were used for detecting the samples from the same batch, in which the operations were performed according to the instructions of the kits, and the Roche and Abbott kits were used with the full-automatic chemiluminescence instruments of their respective companies, and the dilution and detection of the samples were automatically performed by the instruments.

3. Experimental Results

The detection results of the samples from the same batch using the kit of Preparation Example 2, the Roche kit (100 tests/box, Cat. No.: 07143737190) and the Abbott kit were shown in Table 1.

TABLE 1

Determination of concentrations of hepatitis B virus surface antigen in samples P1 to P38

| Sample No. | Abbott (IU/mL) | Roche (IU/mL) | The present invention (IU/mL) |
|---|---|---|---|
| P1 | 444 | 1240 | 439.99 |
| P2 | 794 | 1173 | 1584.89 |
| P3 | 501 | 1034 | 994.78 |
| P4 | 3162 | 11407 | 11416.55 |
| P5 | 631 | 3074 | 1376.94 |
| P6 | 7943 | 14211 | 18805.41 |
| P7 | 32 | 100 | 125.89 |
| P8 | 6310 | 19686 | 15738.38 |
| P9 | 63 | 100 | 125.89 |
| P10 | 8188 | 7930 | 9004.31 |
| P11 | 288 | 445 | 198.27 |
| P12 | 1348 | 1541 | 2110.13 |
| P13 | 12696 | 11977 | 18575.77 |
| P14 | 1872 | 9794 | 3391.13 |
| P15 | 208 | 1170 | 677.70 |
| P16 | 2868 | 8123 | 4306.91 |
| P17 | 9740 | 15792 | 12752.08 |
| P18 | 12656 | 14364 | 11261.68 |
| P19 | 4528 | 3287 | 7654.29 |
| P20 | 12360 | 18142 | 15281.08 |
| P21 | 424 | 738 | 807.52 |
| P22 | 6284 | 10602 | 15878.31 |
| P23 | 964 | 1778 | 1232.46 |
| P24 | 80 | 137 | 158.49 |
| P25 | 10300 | 28063 | 14426.89 |
| P26 | 16 | 25 | 31.62 |
| P27 | 17856 | 20136 | 21193.46 |
| P28 | 500 | 1130 | 591.92 |
| P29 | 176 | 177 | 139.06 |
| P30 | 8116 | 15300 | 12414.66 |
| P31 | 8192 | 10217 | 9340.80 |
| P32 | 1224 | 2920 | 2492.14 |
| P33 | 6284 | 9276 | 8587.02 |
| P34 | 292 | 688 | 829.49 |
| P35 | 7928 | 12090 | 11518.21 |
| P36 | 4704 | 3489 | 4590.60 |
| P37 | 14672 | 16810 | 21535.62 |
| P38 | 612 | 429 | 458.12 |

Figure 2:
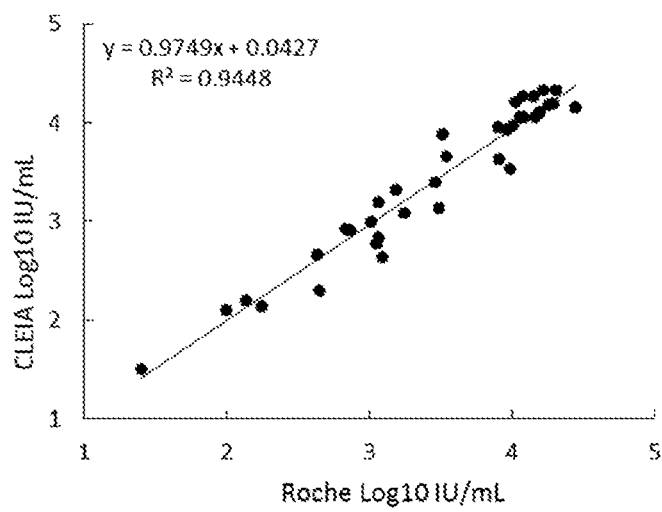
FIG. 2 shows the correlation analysis between the HBsAg quantitative detection result obtained in Example 1 using the kit of Preparation Example 2 and the detection result of commercial reagent (Roche).
Figure 3:
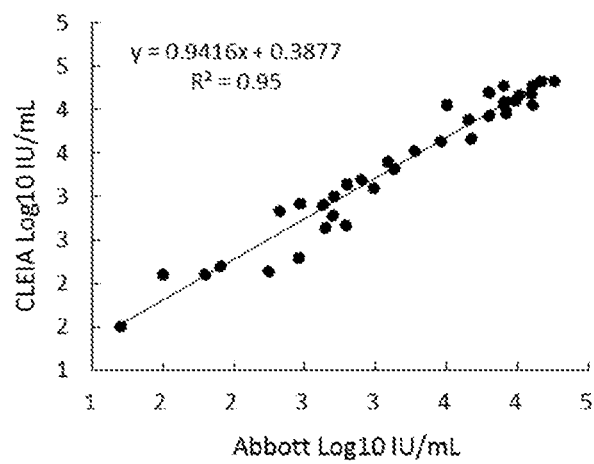
FIG. 3 shows the correlation analysis between the HBsAg quantitative detection result obtained in Example 1 using the kit of Preparation Example 2 and the detection result of commercial reagent (Abbott).

Quantitation correlation analysis was performed on the detection results in Table 1, and the results were shown in FIGS. 2 and 3, respectively. FIG. 2 showed the result of the correlation analysis between the detection results of the kit of Preparation Example 2 and the Roche reagent on the 38 clinical samples, and the result showed that the correlation coefficient $R^2$ of the two was 0.9448. FIG. 3 showed the result of the correlation analysis between the detection results of the kit of Preparation Example 2 and Abbott reagent, and the result showed that the correlation coefficient $R^2$ of the two was 0.95. The above results demonstrated that the kit of the present invention had good detection accuracy.

In addition, the inventors detected 747 clinical HBsAg-positive samples by using the kit of Preparation Example 2, and the concentration distribution range of the samples was calculated. The results were shown in Table 2, in which there were 92.1% of the clinical samples having a concentration within the detection range of 20 to 100,000 IU/mL of the kit of the present invention; in contrast, there were only 25.97% of the samples having a concentration within the detection ranges (0.05 to 250 IU/mL) of conventional HBsAg quantitative detection reagents.

TABLE 2

Concentration distribution ranges of clinical HBsAg-positive samples

| IU/mL | number of samples(n = 747) | % of the total |
|---|---|---|
| <20 | 55 | 7.4 |
| 20 < 250 | 139 | 8.4 |
| 250 < 1000 | 160 | 31.6 |
| 1000 < 10000 | 248 | 33.2 |
| 10000 < 100000 | 141 | 18.9 |
| 100000< | 4 | 0.5 |

COMPARATIVE EXAMPLE 1

Effects of Dissociation Solutions of Different Formulas on the Upper Limit of Detection 1. Experimental reagents: hepatitis B virus surface antigen assay kit (chemiluminescence microparticle immunoassay method) (purchased from Xiamen Wantai Kairui Biotechnology Co., Ltd.); dissociation solution of Preparation Example 1, 40 mM TCEP solution, 600 mM NaCl solution, 2M urea solution and 6M urea.

2. Experimental samples: A sample with a HBsAg concentration of 100,000 IU/mL was 3-fold serially diluted until 0.03 IU/mL with a sample that was negative for both HBsAg and HBsAb.

3. Experimental Steps:

(1) Sample reaction: 20 μL of the sample was added into a reaction tube, followed by addition of 100 μL of the dissociation solution prepared in Preparation Example 1, 2M urea, 6M urea, 600 mM NaCl, 40 mM TCEP solution, respectively. 50 μl of the magnetic particle reagent of the hepatitis B virus surface antigen determination kit (chemiluminescence microparticle immunoassay method) produced by Xiamen Wantai Kairui Biotechnology Co., Ltd. was added, mixed well by shaking, and then reacted in a 37° C. incubator for 15 minutes.

(2) Luminescent label reaction: After step (1) was completed, the chemiluminescence reaction tube was washed twice with PBST washing solution (20 mM PB7.4, 150 mM NaCl, 0.1% Tween-20), and 50 μL of the acridinium ester label reagent of the hepatitis B virus surface antigen assay kit (chemiluminescence microparticle immunoassay method) produced by Xiamen Wantai Kairui Biotechnology Co., Ltd. was added to each well, and reacted in a 37° C. incubator for 10 minutes.

(3) Measurement of luminescence reaction: After step (2) was completed, the chemiluminescence reaction tube was washed 4 times with PBST washing solution (20 mM PB7.4, 150 mM NaCl, 0.1% Tween-20). A Sirius-L single-tube chemiluminescence detector was used, wherein an excitation solution was added by in-situ injection, and light intensity detection was carried out at the same time.

(4) Generation of standard curves for quantitation: After step (3) was completed, linear regression was performed on the measured values and corresponding concentrations of the series of samples obtained by 3-fold gradient dilution of the 100,000 IU/mL HBsAg sample to obtain standard curves for quantitation.

Figure 4:
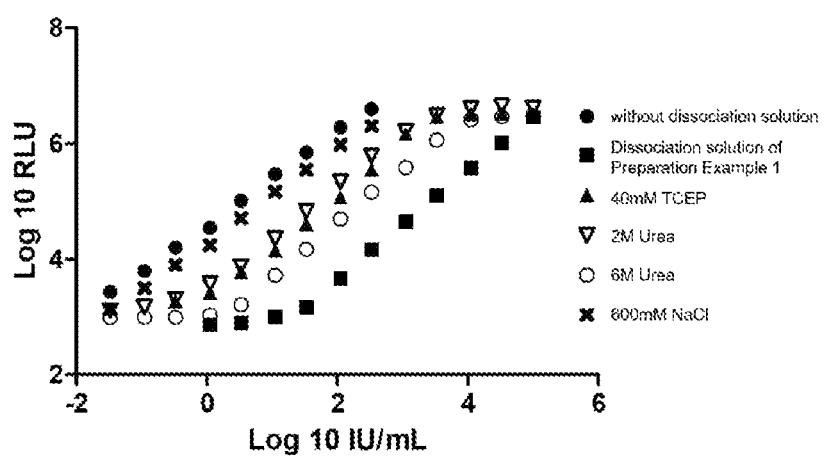
FIG. 4 shows the curves of HBsAg quantitative detection using dissociation solutions of different formulations in Comparative Example 1.

The results were shown in FIG. 4. When 40 mM TCEP or 2M urea was used as the dissociation solution, the detection results thereof were close, and their upper limits of detection were about 3700 IU/mL, which was 10 times higher than that of the conventional HBsAg detection method. In comparison, when the dissociation solution of Preparation Example 1 was used, the upper limit of detection could reach 100,000 IU/mL, which was 400 times higher than that of the conventional HBsAg detection method. The above results showed that the dissociation solution of the present invention could significantly increase the upper limit of detection while ensuring the accuracy of detection, and the linear dynamic range that could be accurately quantified by a single detection could reach 3.5 orders of magnitude, so that tedious dilution treatment was no longer needed for most clinical samples, thereby improving detection efficiency.

Although the specific embodiments of the present invention have been described in detail, those skilled in the art will understand that according to all the teachings that have been disclosed, various modifications and changes can be made to the details, and these changes are all within the protection scope of the present invention. The full scope of the invention is given by the appended claims and any equivalents thereof.

What is claimed is:

1. A kit, comprising a first antibody capable of specifically binding to HBsAg, and a reagent composition, the reagent composition comprising tris(2-carboxyethyl)phosphine hydrochloride (TCEP), urea, a non-ionic surfactant, an inorganic salt and a buffer, wherein:
the TCEP is present in an amount of 1 to 100 mM;
the urea is present in an amount of 0.5 to 8 M;
the non-ionic surfactant is present in an amount of 0 to 10% (v/v),
the inorganic salt is present in an amount of 0.5 to 8 M, and
the buffer is present in an amount of 0 to 200 mM.

2. The kit of claim 1, wherein the reagent composition has one or more of the following characteristics:
(i) the non-ionic surfactant is selected from the group consisting of Chaps, sulfobetaine type surfactants, Triton type detergents, Tween type detergents, and any combination thereof;
(ii) the inorganic salt is selected from $NH_4SO_4$ and NaCl;
(iii) the buffer is a carbonate buffer.

3. The kit of claim 1, wherein the reagent composition comprises:
TCEP, urea, an inorganic salt, a non-ionic surfactant, a buffer, and a balance of water.

4. The kit of claim 1, wherein the kit further comprises a second antibody capable of specifically binding to HBsAg; and optionally the second antibody bears a detectable label.

5. The kit of claim 4, wherein the detectable label is selected from an enzyme, a chemiluminescent reagent, or a fluorescent dye.

6. The kit of claim 1, wherein the kit further comprises a solid support, optionally surface of which is coated with the first antibody.

7. The kit of claim 6, wherein the solid support is a microtiter plate or a magnetic bead.

8. The kit of claim 1, wherein the kit further comprises one or more reagents or devices selected from the group consisting of: a standard; a positive control sample; a negative control sample; a stop solution for stopping a color reaction of substrate catalyzed by enzyme; a blocking solution for inhibiting a non-specific binding; and, a blood collection device.

9. The kit of claim 1, wherein the non-ionic surfactant is selected from SB14, SB 16, Tween-20, Tween-40, Triton X-100, and any combination thereof.

10. The kit of claim 1, wherein TCEP is present in an amount of 10 to 50 mM, and/or, urea is present in an amount of 1 to 8 M.

11. A method for quantitatively detecting the amount of HBsAg in a sample containing HBsAg, comprising the following steps:
(1) contacting the sample with a first antibody capable of specifically binding to HBsAg in a reagent composition to obtain an immune complex, wherein the reagent composition comprises tris(2-carboxyethyl)phosphine hydrochloride (TCEP), urea, a non-ionic surfactant, an inorganic salt and a buffer, wherein:
the TCEP is present in an amount of 1 to 100 mM;
the urea is present in an amount of 0.5 to 8 M;
the non-ionic surfactant is present in an amount of 0 to 10% (v/v),
the inorganic salt is present in an amount of 0.5 to 8 M, and
the buffer is present in an amount of 0 to 200 mM; and
(2) determining the amount of the immune complex obtained in step (1);
wherein the sample is a blood sample.

12. The method of claim 11, wherein the method has one or more of the following characteristics:
(i) the blood sample is selected from whole blood, plasma or serum;
(ii) the blood sample is undiluted;
(iii) the first antibody is coated on the surface of a solid support;
(iv) a step of washing the immune complex to remove unreacted substance is further comprised before step (2).

13. The method of claim 12, wherein, the first antibody is coated on the surface of a microtiter plate or a magnetic bead.

14. The method of claim 11, wherein in step (2), the amount of the immune complex is determined by an immunological detection.

15. The method of claim 14, wherein the immunological detection is an enzyme immunoassay or a chemiluminescence immunoassay.

16. The method of claim 14, wherein the immunological detection is selected from a CLEIA method and a CLIA method.

17. The method of claim 14, in step (2), the amount of the immune complex is detected using a second antibody capable of specifically binding to HBsAg, the second antibody bears a detectable label.

18. The method of claim 17, wherein the detectable label is selected from an enzyme, a chemiluminescent reagent or a fluorescent dye.

* * * * *